(12) United States Patent
Sasayama et al.

(10) Patent No.: US 9,579,239 B2
(45) Date of Patent: Feb. 28, 2017

(54) DISPOSABLE WEARING ARTICLE

(75) Inventors: Kenichi Sasayama, Kanonji (JP); Makoto Ichikawa, Kanonji (JP); Kunihiko Katsuragawa, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 477 days.

(21) Appl. No.: 14/129,051

(22) PCT Filed: Jun. 26, 2012

(86) PCT No.: PCT/JP2012/004117
§ 371 (c)(1),
(2), (4) Date: Dec. 23, 2013

(87) PCT Pub. No.: WO2013/001788
PCT Pub. Date: Jan. 3, 2013

(65) Prior Publication Data
US 2014/0142531 A1    May 22, 2014

(30) Foreign Application Priority Data

Jun. 27, 2011  (JP) ................................. 2011-142354

(51) Int. Cl.
*A61F 13/15*    (2006.01)
*A61F 13/539*   (2006.01)
(Continued)

(52) U.S. Cl.
CPC .......... *A61F 13/539* (2013.01); *A61F 13/495* (2013.01); *A61F 13/496* (2013.01);
(Continued)

(58) Field of Classification Search
CPC ................ A61F 13/49001; A61F 13/53; A61F 2013/530518; A61F 2013/530562; A61F 2013/53051
(Continued)

(56) References Cited

U.S. PATENT DOCUMENTS 5,484,430 A * 1/1996 Osborn, III ........... A61F 13/472
   604/385.21
6,162,204 A * 12/2000 Romare .............. A61F 13/4702
   604/385.01

FOREIGN PATENT DOCUMENTS

JP    2004-329238 A    11/2004
JP    2006-158676 A     6/2006
(Continued)

OTHER PUBLICATIONS

International Search Report and Written Opinion mailed Sep. 25, 2012, in corresponding International Application No. PCT/JP2012/004117 (4 pages).

*Primary Examiner* — Jacqueline Stephens
(74) *Attorney, Agent, or Firm* — Hauptman Ham, LLP

(57) ABSTRACT

Disposable wearing articles having a liquid-absorbent structure which is sufficiently thin to ensure a comfortable wear feeling and adapted to eliminate the possibility that the appearance of the absorbing region after absorption of the bodily fluids might be visually recognized from the outside. A liquid-absorbent structure including absorbent materials is attached to a chassis by means of a liquid-absorbent structure bonding region formed on a skin-facing side. The liquid-absorbent structure bonding region includes opposite end bonding zones serving to fix first and second end segments of the liquid-absorbent structure and opposite lateral bonding zones serving to fix opposite lateral segments of the liquid-absorbent structure and a central non-bonding region is defined by a region surrounded by the opposite end bonding zones and the opposite lateral bonding zones.

18 Claims, 10 Drawing Sheets

(51) Int. Cl.
  *A61F 13/496* (2006.01)
  *A61F 13/495* (2006.01)
  *A61F 13/53* (2006.01)
  *A61F 13/49* (2006.01)

(52) U.S. Cl.
  CPC ......... *A61F 13/49001* (2013.01); *A61F 13/53* (2013.01); *A61F 2013/53051* (2013.01); *A61F 2013/530518* (2013.01); *A61F 2013/530562* (2013.01)

(58) Field of Classification Search
  USPC ............. 604/378, 379, 380, 385.01, 385.101
  See application file for complete search history.

(56) References Cited

FOREIGN PATENT DOCUMENTS

| | | |
|---|---|---|
| JP | 2007-209774 A | 8/2007 |
| JP | 2008-220524 A | 9/2008 |

* cited by examiner

DISPOSABLE WEARING ARTICLE

RELATED APPLICATIONS

The present application is a national phase of International Application Number PCT/JP2012/004117 filed Jun. 26, 2012, and claims priority to Japanese Patent Application Number 2011-142354 filed Jun. 27, 2011.

TECHNICAL FIELD

The present disclosure relates to disposable wearing articles and, more particularly, to disposable wearing articles such as disposable diapers, disposable toilet-training pants, disposable incontinent pants and disposable sanitary pants.

BACKGROUND

Disposable wearing articles including a relatively thin liquid-absorbent structure are known. For example, JP 2006-158676 A (PTL 1) discloses a disposable wearing article including a liquid-permeable topsheet lying on a skin-facing side, a backsheet lying on a non-skin-facing side and a liquid-absorbent structure containing water-absorbent polymer particles only.

CITATION LIST

Patent Literature

{PTL 1}
JP 2006-158676 A

SUMMARY

Technical Problem

In the wearing article disclosed in PTL 1, the absorbing region adapted to absorb and to contain bodily fluids is formed of the water-absorbent polymer particles only. In consequence, the wearing article is sufficiently thin to improve the wear feeling provided by the article and ensures bodily fluids to be quickly absorbed.

However, the inventor (s) have recognized that the absorbing region formed of the water-absorbent polymer particles only or additionally containing fluff wood pulp at an extremely low percentage may result in poor shape retention and distinguishable change in shape as well as in thickness of the absorbent structure in comparison to the case in which the content of the water-absorbent polymer particles is substantially equal to the content of the fluff wood pulp. The fluff wood pulp is tinged with white and, even when bodily fluids are absorbed by the fluff wood pulp, such bodily fluids would not be visually recognized so easily through other sheets. In contrast, the water-absorbent polymer particles are slightly tinged with white or transparent and the absorbed bodily fluids might be visually recognized with relative ease from the outside. Therefore, if the absorbing region with the composition disclosed in PTL 1 is attached to the backsheet lying outside the absorbing region with adhesives, the change in the appearance inclusive of the shape, the thickness and the color of the absorbing region occurring before and after absorption of the bodily fluids may be easily visually recognized from the outside and result in disfigurement.

Solution to Problem

Some embodiments of the present invention provide a disposable wearing article having a longitudinal axis and a transverse axis being orthogonal to the longitudinal axis. The article includes a chassis and a liquid-absorbent structure. The chassis includes a skin-facing side, a non-skin-facing side, a front waist region, a rear waist region and a crotch region extending between the front and rear waist regions. The liquid-absorbent structure is attached to the skin-facing side of the chassis to lie in the crotch region.

The liquid-absorbent structure has front and rear ends extending in the direction of the transverse axis and opposite side edges extending in the direction of the longitudinal axis between the front and rear ends. The liquid-absorbent structure is attached to the chassis by means of liquid-absorbent structure bonding region. The liquid-absorbent structure bonding region includes opposite end bonding zones and opposite lateral bonding zones, and a central non-bonding region is surrounded by the opposite end bonding zones and the opposite lateral bonding zones. A central area of the liquid-absorbent structure corresponding to the central non-bonding region is free of direct attachment to the chassis.

DESCRIPTION OF EMBODIMENTS

First Embodiment

Figure 1:
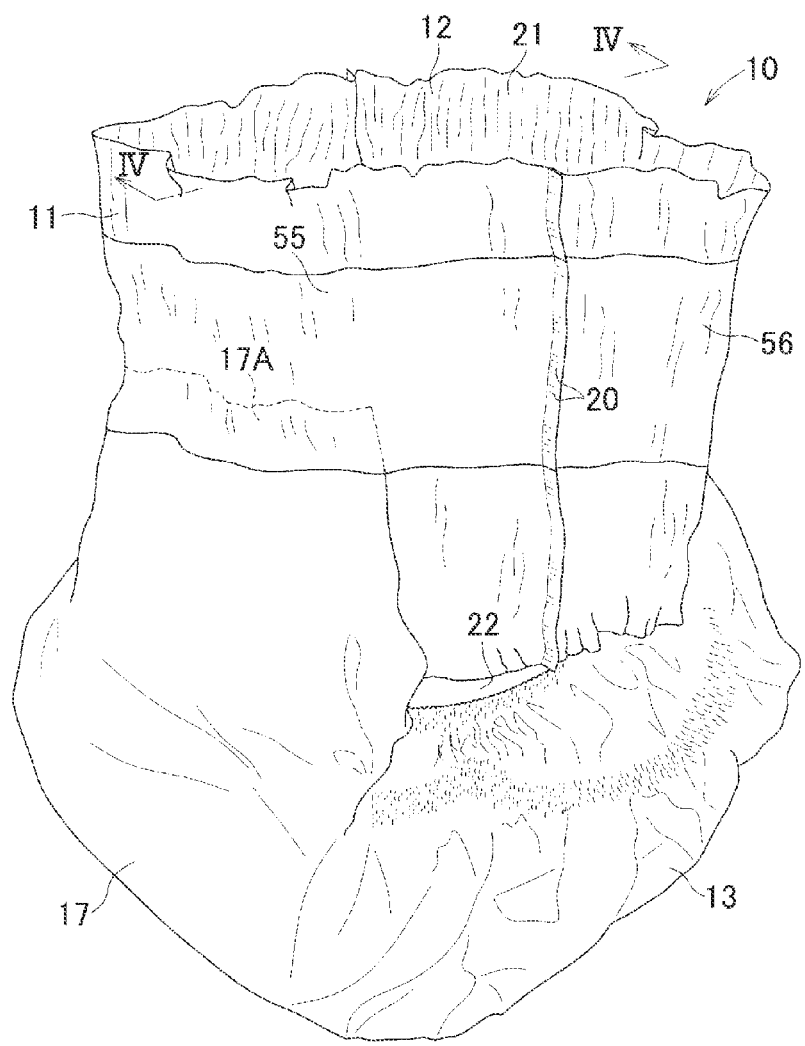
FIG. 1 is a perspective view of a disposable diaper as one example of disposable wearing articles according to a first embodiment of this invention.
Figure 2:
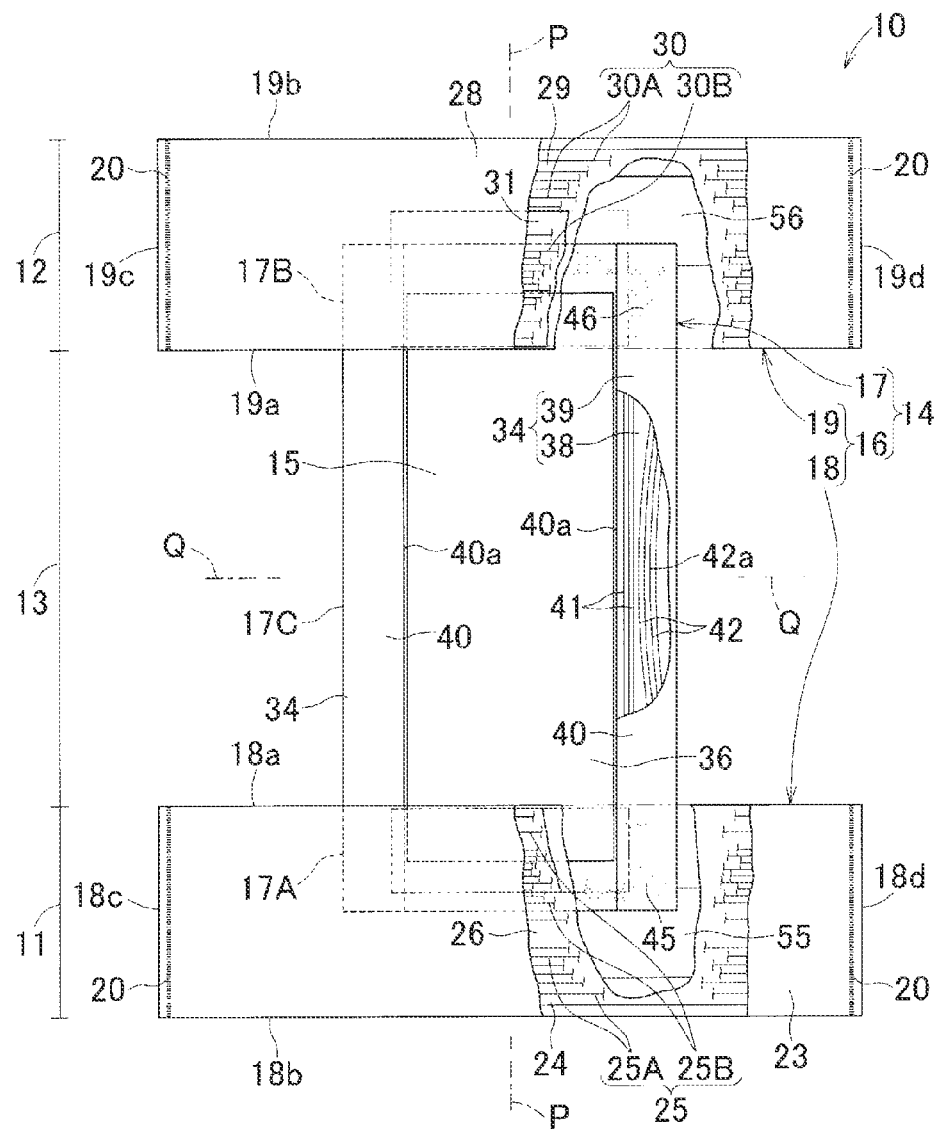
FIG. 2 is a partially cutaway developed plan view of the diaper developed in the front-back direction after side seams have been peeled off as viewed from the inner side (skin-facing side) of the diaper.
Figure 3:
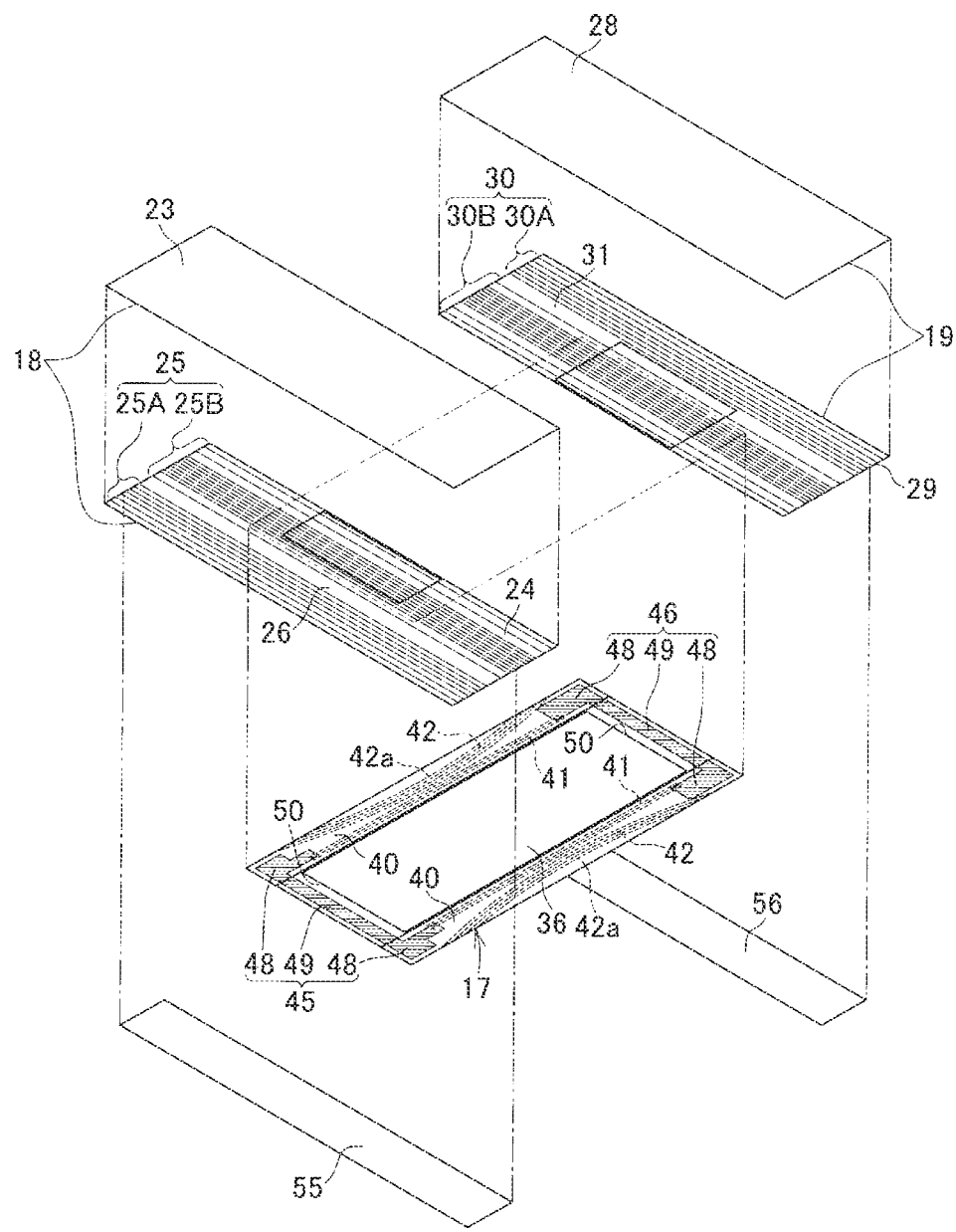
FIG. 3 is an exploded perspective view of the diaper.

As illustrated in FIGS. 1 to 3, a disposable diaper 10, one example of disposable wearing articles according to some embodiments of this invention, has a longitudinal axis P and a transverse axis Q and shaped symmetrically about the longitudinal axis P. The diaper 10 includes a chassis 14 having a front waist region 11, a rear waist region 12 and a crotch region 13 extending in a direction of the longitudinal axis P (longitudinal direction) between the front and rear waist regions 11, 12, and a liquid-absorbent structure 15 attached to a skin-facing side of at least the crotch region 13.

The chassis 14 has a skin-facing side, a non-skin-facing side opposite to the skin-facing side, an annular elasticized waist panel 16 extending circumferentially about the waist and a crotch body 17 attached to the non-skin-facing side of the elasticized waist panel 16. The elasticized waist panel 16 includes a front waist panel 18 defining the front waist region 11 and a rear waist panel 19 defining the rear waist region 12.

The front waist panel 18 intersects the crotch body 17 and has a transversely longer rectangular shape contoured by an inner end 18a extending in a direction of the transverse axis Q (transverse direction), an outer end 18b spaced apart from and opposed to the inner end 18a in the direction of the longitudinal axis P and extending in the direction of the transverse axis Q and opposite side edges 18c, 18d extending in the direction of the longitudinal axis P between the inner and outer ends 18a, 18b.

The rear waist panel 19 is substantially the same as the front waist panel 16 in shape as well as in size and intersects the crotch body 17. The rear waist panel 19 has a transversely longer rectangular shape contoured by an inner end 19a extending in the direction of the transverse axis Q, an outer end 19b spaced apart from and opposed to the inner end 19a in the direction of the longitudinal axis P and extending in the direction of the transverse axis Q and opposite side edges 19c, 19d extending in the direction of the longitudinal axis P between the inner and outer ends 19a, 19b.

The opposite side edges 18c, 18d of the front waist panel 18 and the opposite side edges 19c, 19d of the rear waist panel 19 are joined together with side seams 20 arranged intermittently in the direction of the longitudinal axis P to define a waist-opening 21 and a pair of leg-openings 22 (See FIG. 1). The side seams 20 are formed with, for example, various kinds of thermal adhesion techniques such as hot embossing, ultrasonic treatment and the like.

The front waist panel 18 includes a first inner sheet 23 lying on the skin-facing side and a first outer sheet 24 lying on the non-skin-facing side. The first inner and outer sheets 23, 24 are formed of a liquid-impermeable SMS (spun bonded/melt blown/spun bonded) nonwoven fabric or a spun bonded nonwoven fabric each having a mass per unit area in a range of about 15 to 30 g/m² or a laminate of such nonwoven fabric and plastic sheet. These two sheets 23, 24 are bonded to each other with hot melt adhesives intermittently applied to at least one of these two sheets 23, 24 or by the aforementioned thermal adhesion techniques.

A plurality of strand- or string-like front waist elastics 25 extending in the direction of the transverse axis Q are disposed between these two sheets 23, 24. The front waist panel 18 is stretchable at least in the direction of the transverse axis Q under the effect of the front waist elastics 25. In this regard, these two sheets 23, 24 may be bonded to each other only with hot melt adhesives applied to the front waist elastics 25 on substantially entire peripheral surfaces thereof.

The front waist elastics 25 include front upper waist elastics 25A extending in the direction of the transverse axis Q along the outer end 18b and front lower waist elastics 25B extending in the direction of the transverse axis Q along the inner end 18a. The front lower waist elastics 25B are arranged more densely than the front upper waist elastics 25A and an inelastic region 26 in which no elastic is arranged is defined between the front upper and lower waist elastics 25A, 25B.

The rear waist panel 19 includes a second inner sheet 28 lying on the skin-facing side and a second outer sheet 29 lying on the non-skin-facing side. The second inner and outer sheets 28, 29 are formed of a liquid-impermeable SMS (spun bonded/melt blown/spun bonded) nonwoven fabric or a spun bonded nonwoven fabric each having a mass per unit area in a range of about 15 to about 30 g/m² or a laminate of such nonwoven fabric and plastic sheet. These two sheets 28, 29 are bonded to each other with hot melt adhesives applied to at least one of these two sheets 28, 29 or by the aforementioned thermal adhesion techniques.

A plurality of strand- or string-like rear waist elastics 30 extending in the direction of the transverse axis Q are disposed between these two sheets 28, 29. The rear waist panel 19 is stretchable at least in the direction of the transverse axis Q under the effect of the rear waist elastics 30. In this regard, these two sheets 28, 29 may be bonded to each other only with hot melt adhesives applied to the respective rear waist elastics 30 on substantially entire peripheral surfaces thereof.

The rear waist elastics 30 include rear upper waist elastics 30A extending in the direction of the transverse axis Q along the outer end 19b and rear lower waist elastics 30B extending in the direction of the transverse axis Q along the inner end 19a. The rear lower waist elastics 30B are arranged more densely than the rear upper waist elastics 30A and inelastic region 31 in which no elastic is arranged is defined between the rear upper and lower waist elastics 30A, 30B.

The crotch body 17 has a substantially rectangular shape being longer in the direction of the longitudinal axis P and includes a front end segment 17A attached to the non-skin-facing side (outer surface) of the front waist panel 18, a rear end segment 17B attached to the non-skin-facing side of the rear waist panel 19 and an intermediate segment 17C extending in the direction of the longitudinal axis P between the front and rear end segments 17A, 17B. The crotch body 17 further includes a crotch layered sheet 34, the liquid-absorbent structure 15 placed on the skin-facing side (inner surface) of the crotch layered sheet 34 and a body side liner 36 formed of a liquid-permeable sheet used to wrap the liquid-absorbent structure 15.

While the diaper 10 is configured with the chassis 14 including the separately prepared front and rear waist regions 11, 12 and the crotch region 13 in this embodiment, it is also possible to configure the diaper 10 with the chassis 14 in which the respective regions 11, 12 and 13 are integrally formed so long as advantageous effects of some embodiments of this invention to be described later in detail may be obtained. In this case, the liquid-absorbent structure 15 may be disposed between the liquid-permeable topsheet lying on the skin-facing side of the chassis 14 and a liquid-impermeable backsheet lying on the non-skin-facing side.

The crotch layered sheet 34 is formed from inner and outer crotch sheets 38, 39 at least one of which is formed of a liquid-impermeable fibrous nonwoven fabric sheet or a plastic film. These inner and outer crotch sheets 38, 39 are bonded to each other with hot melt adhesives (not shown) applied to the inner surface of one of these sheets 38, 39 and opposite lateral portions of these sheets 38, 39 are folded inward to form a pair of lateral elastic segments 40 extending in the longitudinal direction.

The respective lateral elastic segments 40 are provided with a plurality of strand- or string-like first and second leg elastics 41, 42 and the respective lateral elastic segments 40 are elasticized at least in the direction of the longitudinal axis P. The first leg elastics 41 rectilinearly extend in the direction of the longitudinal axis P along inner side edges 40a of the respective lateral elastic segments 40 and the second leg elastics 42 curve concavely inward in the intermediate segment of the crotch region 13 and extend in a curved state toward the front and rear waist regions 11, 12. The first and second leg elastics 41, 42 are disposed and attached under tension in the direction of the longitudinal axis P between the inner and outer crotch sheets 38, 39 with hot melt adhesives (not shown) applied to the inner surface of one of the inner and outer crotch sheets 38, 39.

Middle segments 42a of the respective second leg elastics 42 convexly curve toward the longitudinal axis P and tensile stress of these elastics are locally enhanced. In consequence, the lateral elastic segments 40 in the vicinity of the middle segments thereof facing the wearer's thighs come in close contact with the wearer's body and thereby effectively prevent body waste from leaking sideways beyond the leg-openings' peripheral edges.

Figure 4:
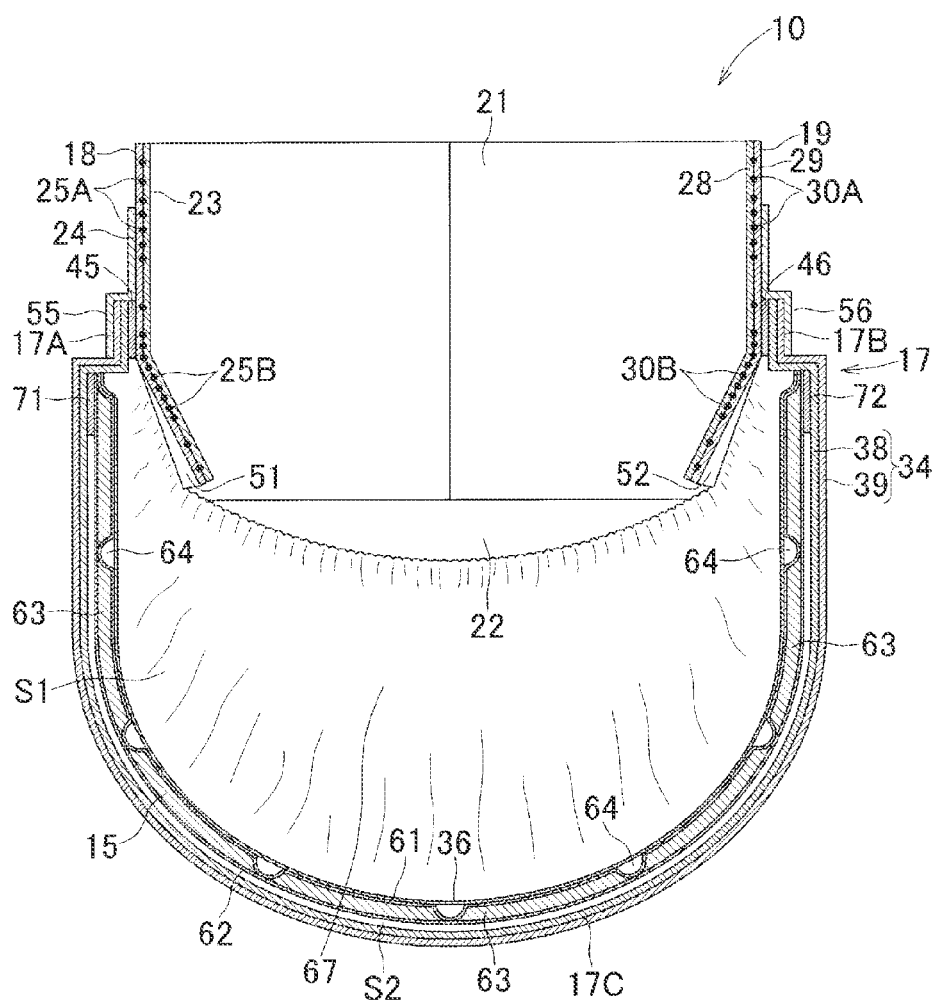
FIG. 4 is a sectional view taken along line IV-IV in FIG. 1.

The crotch body 17 is attached at the front end segment 17A and the rear end segment 17B thereof to the respective outer surfaces of the front and rear waist panels 18, 19 in a front bonding region 45 and a rear bonding region 46 formed of hot melt adhesives applied to the skin-facing side of the front end segment 17A and the rear end segment 17B, respectively. As illustrated in FIG. 4, the front and rear end segments 17A, 17B of the crotch body 17 may be attached to the outer surfaces of the front and rear waist panels 18, 19 in this manner to ensure a body waste collecting space S1 be larger than the case in which these front and rear end segments 17A, 17B are attached to the inner surface of the front and rear waist panels 18, 19. It is also possible to attach one of the front and rear end segments 17A, 17B to the inner surface of the front waist panel 18 or the rear waist panel 19 so long as the body waste collecting space S1 of a desired volume may be ensured.

Both the front and rear bonding regions 45, 46 have U-shapes opening toward the crotch region 13 and respectively include opposite lateral portions 48 and middle portions 49 extending in the direction of the transverse axis Q between the respective opposite lateral portions 48. The middle portions 49 lie outboard of the region in which the liquid-absorbent structure 15 is present as viewed in the direction of the longitudinal axis P. Between the respective opposite lateral portions 48 and the respective middle portions 49, non-bonding regions 50 which are not coated with hot melt adhesives are defined. While the opposite lateral portions 48 in the front bonding region 45 are stepwise and the opposite lateral portions 48 in the rear bonding region 46 are rectangular in this embodiment, these opposite lateral portions 48 are not limited to such shapes but these opposite lateral portions 48 may have various shapes such as stepwise shape, rectangular shape or curved shape.

As illustrated in FIG. 4, the non-bonding regions 50 defined between the front and rear bonding regions 45, 46 make it possible to form front and rear pockets (spaces) 51, 52 between the front and rear waist panels 18, 19 and the crotch body 15. Formation of the front and rear pockets 51, 52 makes it possible to enlarge the body waste collecting space S1 and, in consequence, it is possible for the crotch body 17 to have a configuration being suspended from the elastic waist panel 16 under the influence of a mass of body waste.

The front and rear end segments 17A, 17B of the crotch body 17 are provided with cover sheets 55, 56 attached thereto to cover them. Specifically, the cover sheets 55, 56 are formed of a fibrous nonwoven fabric or plastic sheet having a mass per unit area in a range of about 10 to about 30 g/m$^2$ and attached to the non-skin-facing side of the front and rear waist panels 18, 19 with hot melt adhesives (not shown) to intersect with the front and rear end segments 17A, 17B. By covering the front and rear end segments 17A, 17B with the cover sheets 55, 56 in this manner, fingers of the wearer or a helper are unlikely caught by the front and/or rear end segments 17A, 17B when the wearer or the helper grips the front and rear waist panels 18, 19 with his or her fingers to put the diaper 10 on the wearer's body. In addition, the cover sheets 55, 56 attached to the front and rear end segments 17A, 17B increase stiffness sufficiently to prevent the sheet members from being partially broken and to enable the wearer or the helper to pull up these front and rear end segments 17A, 17B with the fingers stably.

Figure 5:
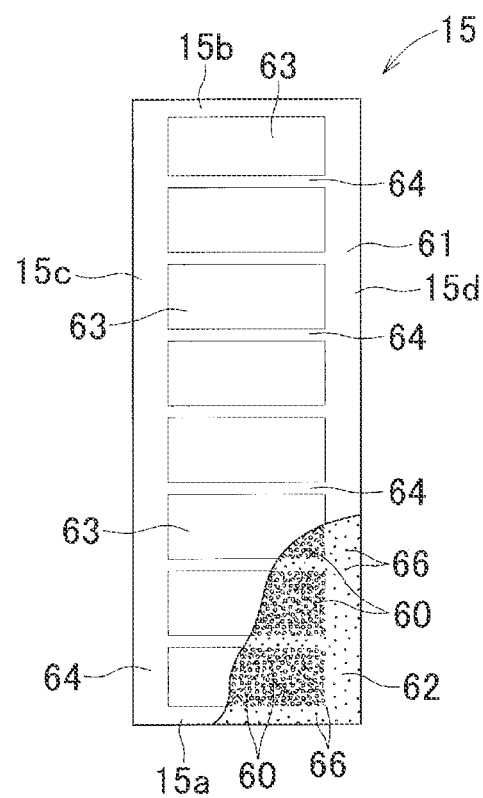
FIG. 5 is a partially cutaway plan view of a liquid-absorbent structure.

As illustrated in FIG. 5, the liquid-absorbent structure 15 is contoured by a front end 15a extending on the side of the front waist region 11 in the direction of the transverse axis Q, a rear end 15b extending on the side of the rear waist region 12 in the direction of the transverse axis Q and opposite side edges 15c, 15d extending in the direction of the longitudinal axis P between the front and rear ends 15a, 15b.

The liquid-absorbent structure 15 includes absorbent materials 60 formed of only water-absorbent polymer particles which are water-soluble and have water-absorbability ten times or more of own mass, an upper sheet 61 formed of a water-permeable fibrous nonwoven fabric lying on the skin-facing side and having a mass per unit area in a range of about 8.0 to about 15.0 g/m$^2$, preferably in a range of about 10.0 to about 12.0 g/m$^2$, and a lower sheet 62 formed of a water-permeable or a poorly water-permeable SMS fibrous nonwoven fabric lying on the non-skin-facing side and having a mass per unit area in a range of about 8.0 to about 15.0 g/m$^2$, preferably in a range of about 10.0 to about 12.0 g/m$^2$.

The liquid-absorbent structure 15 further has at least one absorbing region 63. In this embodiment, a plurality of absorbing regions 63 is defined in substantially rectangular sub-regions spaced apart from each other in the direction of the longitudinal axis P and respectively containing the absorbent materials 60 therein and a sealing region 64 surrounding the absorbing regions 63 and substantially not containing the absorbent materials 60 therein. While the absorbing region 63 is divided into eight sub-regions in this embodiment, the number and the area of the sub-regions may be appropriately selected depending on the absorptive capacity required for the liquid-absorbent structure 15. For example, the absorbing region 63 may be divided into eight or more sub-regions or may be defined as the only absorbing region within the entirety of the liquid-absorbent structure 15. It is also possible for the absorbent materials 60 to contain, in addition to the superabsorbent polymer particles, other materials, such as fluff wood pulp or thermoplastic fibers, at a relatively low ratio so long as the advantageous effects of some embodiments of this invention to be described later may be obtained.

In the absorbing regions 63, the water-absorbent polymer particles having a mass per unit area in a range of about 30 to about 300 g/m$^2$, preferably in a range of about 40 to about 280 g/m$^2$ are attached substantially uniformly with hot melt adhesive 66 applied to the inner surface of the lower sheet 62. In the absorbing regions 63, it is preferable that the upper sheet 61 and the lower sheet 62 are partially bonded or not bonded at all to each other.

In the sealing region 64 defined in the spaces between the adjacent absorbing regions 63 and a region extending along the outer peripheral edge of the liquid-absorbent structure 15, the upper and lower sheets 61, 62 are bonded to each other with hot melt adhesive 66.

The absorbent materials 60 of the liquid-absorbent structure 15 is formed only from the water-absorbent polymer particles or with a relatively low ratio of other materials as has been described and, in consequence, the absorbent materials 60 is thinner and more adaptable to movements of the crotch body 17 than the liquid-absorbent materials formed of a mixture of the water-absorbent polymer particles and a relatively large amount of the fluff wood pulp.

The arrangement such that the upper and lower sheets 61, 62 are stably bonded to each other in the sealing region 64 ensures a required peel strength and a flexibility higher than the case in which the upper and lower sheets 61, 62 are bonded to each other over whole inner surfaces thereof. The water-absorbent polymer particles are evenly secured in the respective absorbing regions 63 and, in consequence, a distribution of the water-absorbent polymer particles is unlikely disturbed due to the movement or posture of the wearer.

Alternatively, it is also possible to fill the respective absorbing regions 63 with the water-absorbent polymer particles to an upper limit of acceptable amount so that the water-absorbent polymer particles are partially not secured with hot melt adhesive 66 and movably wrapped within the respective absorbing regions 63. In such a case, each of the absorbing regions 63 may be formed in a bag-like state and an upper limit of the total amount of the water-absorbent polymer particles containable within these bag-like absorbing regions 63 is about 400 g/m$^2$. In such an alternative case, the sealing region 64 functions as sealing means adapted to seal the peripheral edges of the respective absorbing regions 63 and thereby to prevent the movable water-absorbent polymer particles from tumbling out of the bag-like absorbing regions 63. However, there is a possibility that a part of the water-absorbent polymer particles at a mass per unit area lower than that required for the absorbing regions 63 may be moved into the sealing region 64 in the course of the manufacturing process.

A thickness dimension of the midsection of the crotch body 17 including the liquid absorbent structure 15 (thickness dimension of the midsection of the crotch region 13 in the chassis 14) is specifically about 5.0 mm or less. Cantilever bending resistance thereof is in a range of 15 to 140 mm.

<Measuring Method for Thickness>

The thickness of the crotch body 17 in the midsection thereof can be measured with use of Thickness Tester (one of the PEACOCK accurate measuring instruments manufactured by OZAKI MFG. CO., LTD.) (probe diameter: in a range of 10 to 20 mm).

<Measuring Method for Cantilever Bending Resistance>

In accordance with JIS L1096 Cantilever Method, test pieces (having a dimension of 50 mm in the direction of the transverse axis Q and a dimension of 150 mm in the direction of the longitudinal axis P) were cut out from the midsections of the crotch body 17 of the diaper 10 and measurements were conducted on the skin-facing side and the non-skin-facing side of the respective test pieces. Three measurements were made and averaged.

So long as a required absorbing capacity and a required flexibility in the thickness direction are ensured, the liquid-absorbent structure 15 is not necessarily divided into the absorbing region(s) 63 and the sealing region 64 but may also be in a configuration in which a single absorbing region 63 is formed as the only absorbing region within the whole area of the liquid-absorbent structure 15.

As illustrated in FIG. 4, the liquid-absorbent structure 15 has a sheet-like configuration which is sufficiently thin and sufficiently low in stiffness to conform to the movements of the wearer's body and to be kept in a state of being suspended within the crotch body 17 during use. Furthermore, the liquid-absorbent structure 15 is sufficiently flexible to conform to the movements of the crotch layered sheet 34. Specifically, the liquid-absorbent structure 15 takes on a configuration curved along a leakage-barrier 67 under extension of the lateral elastic segments 40 and the crotch body 17 as a whole takes on a configuration like a bulging bag already before bodily fluids are excreted.

Figure 6:
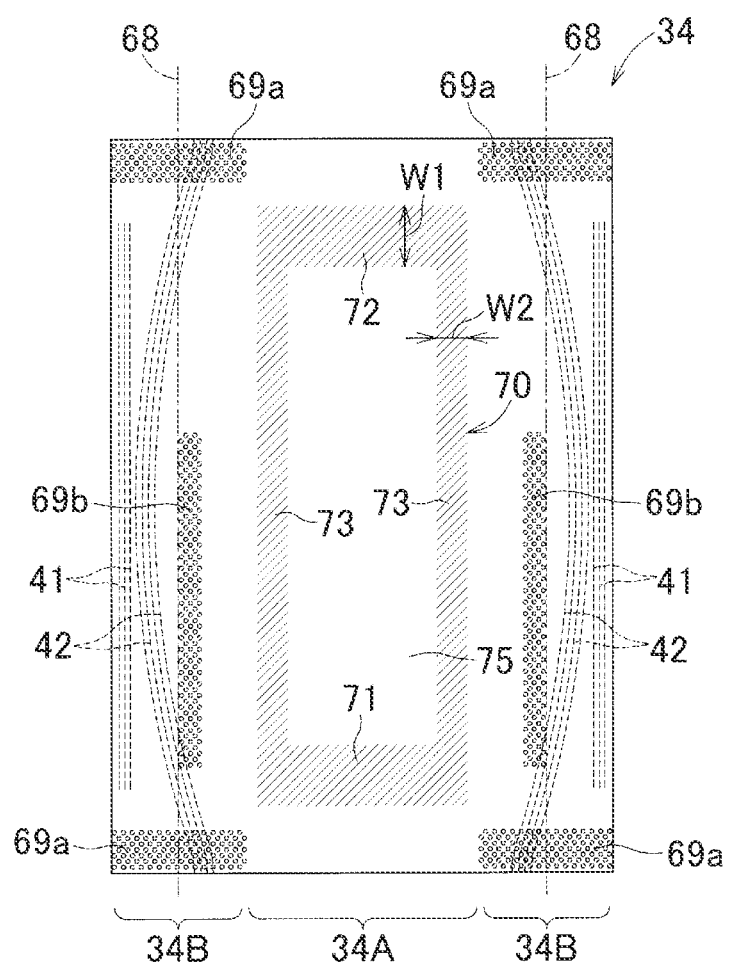
FIG. 6 is an unfolded plan view of a crotch layered sheet.
Figure 7:
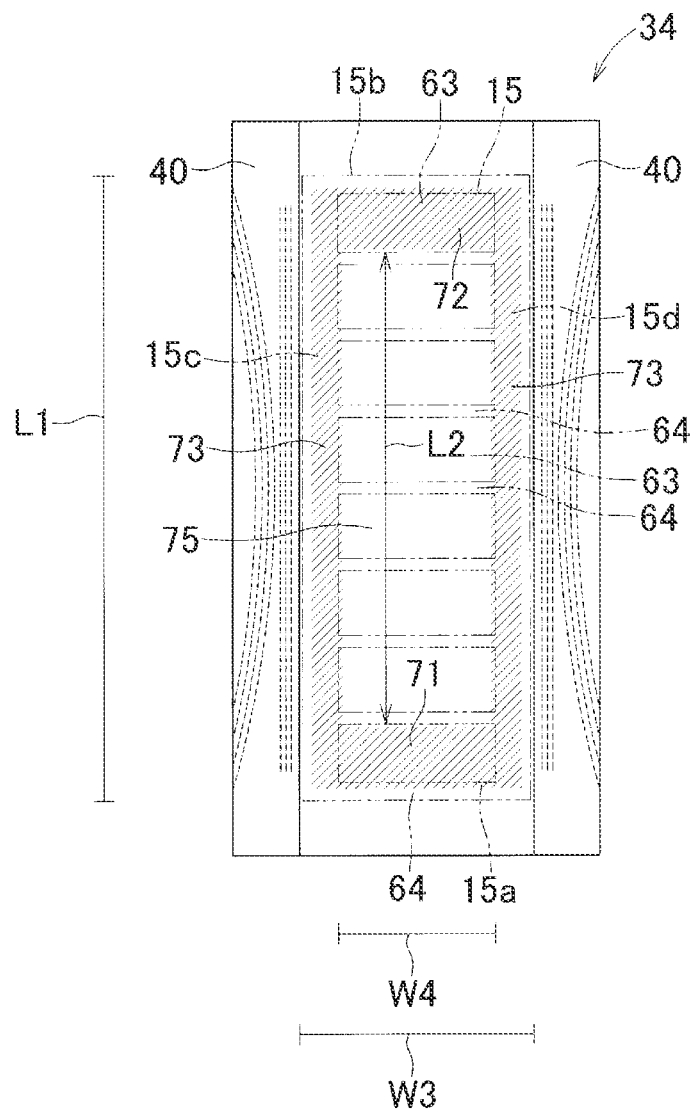
FIG. 7 is a folded plan view of the crotch layered sheet.

FIG. 6 is a developed plan view of the crotch layered sheet 34 and FIG. 7 is a folded plan view of the crotch layered sheet 34. For convenience of illustration, the liquid-absorbent structure 15 is indicated by imaginary lines in FIG. 7.

As illustrated in FIG. 6, the crotch layered sheet 34 has a central segment 34A and opposite lateral segments 34B lying on both sides of the central segment 34A. The opposite lateral segments 34B are folded inward along fold lines 68 extending in the direction of the longitudinal axis P and attached by means of lateral elastics bonding regions 69a, 69b and thereby the lateral elastic segments 40 are formed.

The central segment 34A of the crotch layered sheet 34 is formed on the inner surface thereof with the liquid-absorbent structure bonding region 70 in which the liquid-absorbent structure 15 is to be attached to the crotch layered sheet 34. The liquid-absorbent structure bonding region 70 is provided in the form of a continuous rectangular frame contoured by opposite end bonding zones 71, 72 opposed to each other in the direction of the longitudinal axis P and extending in the direction of the transverse axis Q, and a pair of lateral bonding zones 73 extending in the direction of the longitudinal axis P. A central non-bonding region 75 is surrounded by the opposite end bonding zones 71, 72 and the opposite lateral bonding zones 73. In this regard, the hot melt adhesive adapted to form the opposite lateral elastics bonding regions 69a, 69b and the hot melt adhesive adapted to form the liquid-absorbent structure bonding region 70 may be applied to the same surface substantially in the same step in the course of the diaper manufacturing process to simplify the manufacturing process in comparison with the case in which application of the hot melt adhesives are carried out in different steps. While the liquid-absorbent structure bonding region 70 is illustrated to be slightly spaced inward from the outer peripheral edge of the liquid-absorbent structure 15, it is possible for the liquid-absorbent structure bonding region 70 to have a sufficiently large size to come nearly in contact with the outer peripheral edge of the liquid-absorbent structure 15 to fix the liquid-absorbent structure 15 more securely.

The absorbent materials 60 of the liquid-absorbent structure 15 contains the water-absorbent polymer particles only or additionally contains fluff wood pulp at a slight content percentage and when the water-absorbent polymer particles in the absorbing regions 63 absorbs bodily fluids, the water-absorbent polymer particles are colored in the color of bodily fluids. At the same time, thickness and configuration of the absorbing regions 63 as a whole are changed and slightly uneven surfaces are formed between the absorbing regions 63 and the sealing region 64. When substantially entire area of the liquid-absorbent structure 15 is attached to the crotch layered sheet 34 and particularly the liquid-absorbent structure 15 is attached to the crotch layered sheet 34 in the central area of the crotch region 13, a color contrast between the absorbing regions 63 containing bodily fluids and the sealing region 64 containing no bodily fluids becomes significant to bring the presence of bodily fluids into clear view and thereby possibly to disfigure the diaper 10.

In the arrangement of this embodiment, however, the central non-bonding region 75 is defined between the opposite end bonding zones 71, 72 and the opposite lateral segment bonding regions 72 and therefore the central area of the liquid-absorbent structure 15 is not attached to the crotch layered sheet 34 (i.e., the central area of the liquid-absorbent structure 15 corresponding to the central non-bonding region 75 is free of direct attachment to the chassis 14). In consequence, the central area of the liquid-absorbent structure is kept spaced apart from the crotch layered sheet 34 during use of the diaper 10. Specifically, a space S2 is formed between the liquid-absorbent structure 15 and the crotch layered sheet 34 as illustrated in FIG. 4 and the configuration of the absorbing regions 63 containing therein the water-absorbent polymer particles and having absorbed bodily fluids is unlikely easily visually recognized from the outside. In this regard, the term "configuration" used herein includes shape, thickness and coloring due to bodily fluids which might be visually recognized from the outside.

The central area of the liquid-absorbent structure 15 is not bonding to the crotch layered sheet but the outer peripheral edge segment is attached to the crotch layered sheet 34 with the liquid-absorbent structure bonding region 70. Consequently, the liquid-absorbent structure 15 is unlikely unfastened from the crotch layered sheet 34 during use of the diaper 10. A width dimension W1 (in the direction of the longitudinal axis P) of the respective end bonding zones 71, 72 is in a range of about 40 to about 60 mm and a width dimension W2 (in the direction of the transverse axis Q) of the respective lateral bonding zones 73 is in a range of about 10 to about 12 mm, i.e., the opposite end bonding zones 71, 72 are wider than the opposite lateral bonding zones 73. Therefore, the liquid-absorbent structure 15 is secured in the opposite end bonding zones 71, 72 more stably than in the opposite lateral bonding zones 73 and even when the weight of the liquid-absorbent structure 15 increases due to absorption of bodily fluids, the first and second end segments 15a, 15b might not be peeled off from the inner surface of the crotch layered sheet 34 and/or the liquid absorbent structure 15 is unlikely to be displaced within the diaper 10 due to the increased weight of the liquid-absorbent structure 15. The opposite lateral bonding zones 73 extend continuously in the direction of the longitudinal axis P and thereby side edge zones of the respective absorbing regions 63 are stably attached to the crotch body 15 so that bodily fluids would not leak out beyond these side edge zones.

The liquid-absorbent structure bonding region 70 may be formed with use of various thermal sealing means or adhesives and, when it is formed with adhesives, for example, hot melt adhesive of a mass per unit area in a range of about 3.0 to about 20 g/m² may be used. While hot melt adhesive is applied in a planar pattern in this embodiment, it is possible to apply hot melt adhesive in various patterns such as Q-, spiral-, dotted- and grid-pattern. An area of bonding area defined by the liquid-absorbent structure bonding region 70, more specifically, an area of the range (sub-region) in which the liquid-absorbent bonding region 70 overlaps the absorbing regions 63 is preferably in a range of about 0 to about 50% of the total area of the absorbing regions 63. This is because, by limiting the overlapping area to such range, an outer shape of the absorbing regions 63 as a whole is unlikely visually recognized from the outside of the diaper 10 and the diaper 10 is unlikely distinctly disfigured. In this regard, the area of the liquid-absorbent structure bonding region 70 overlapping the absorbing regions 63 is about 0% of the area of the absorbing regions 63 when, for example, the liquid-absorbent structure bonding region 70 is provided in the shape of the continuous rectangular frame so as not to overlap the absorbing regions 63 or when the liquid-absorbent structure bonding region 70 is provided in the shapes other than the rectangular frame so as not to overlap the absorbing regions 63.

Dimensions L2, W4 of the central non-bonding region 75 respectively in the directions of the longitudinal axis P and the transverse axis Q are preferably about 50% or more, more specifically in a range of about 50 to about 99%, of dimensions L1, W3 of the liquid-absorbent structure 15 respectively in the directions of the longitudinal axis P and the transverse axis Q. If such percentage is 50% or less, the area over which the central non-bonding region 75 is formed will be relatively small and, in consequence, the configuration of the absorbing regions 63 might be visually recognized with ease from the outside and, in contrast, if such percentage is 99% or more (i.e., the overall size of the central non-bonding region 75 is substantially equal to the overall size of the liquid-absorbent structure 15), the liquid-absorbent structure 15 might not be stably attached and the liquid-absorbent structure 15 might be displaced during use of the diaper 10.

While the liquid-absorbent structure bonding region 70 partially covers the absorbing regions 63, it is preferable that the liquid-absorbent structure bonding region 70 does not fully cover one or more absorbing regions 63 and does not overlap the sealing region 64 defined between these adjacent absorbing regions 63. This is because if the respective absorbing regions 63 as a whole are attached to the crotch layered sheet 34 by means of the liquid-absorbent structure bonding region 70, the outer shapes of the respective rectangular absorbing regions might be distinctly visible from the outside and the diaper 10 might be significantly disfigured.

In order that the configuration of the absorbing regions 63 having absorbed bodily fluids may not be easily visible from the outside, a total luminous transmittance of the crotch layered sheet 34 (or the sheet members forming the crotch region 13 of the chassis 14) is preferably about 40% or less. This is because, at the total luminous transmission of about 40% or less, the configuration of the absorbing regions 63 in the central non-bonding region 75 is not easily visible from the outside and the diaper 10 would not be distinctly disfigured. In addition to restriction of the total luminous transmittance, respective surfaces of the plastic sheets used as the inner and outer crotch sheets 38, 39 of the crotch layered sheet 34 may be printed, with use of various printing means such as flexo printing, ink jet printing or gravure printing with colors, patterns, letters or characters or paint and/or pigment may be mixed in the primary material of the plastic sheet to color this or a content of inorganic filler such as calcium carbonate may be increased to enhance white color of the sheet material.

<Measuring Method for Total Luminous Transmittance>

Transmission Colorimeter A300/ZE-2000 manufactured by Nippon Denshoku Industries Co., Ltd. was used to measure the total luminous transmission in accordance with JIS K7105 General Optical Property-Luminous Transmission Measuring Method A. Measurements were conducted by a procedure as follows: the crotch layered sheet 34 was cut to obtain test pieces of 50×50 mm, the test piece was held by the test piece clip and the lid was closed. The start key of the colorimeter was pushed to start the measurement, and TT-value displayed was recorded. Similar measurements were conducted three times and three TT-values were averaged to obtain the total luminous transmittance (%) of this sheet material.

Second Embodiment

Figure 8:
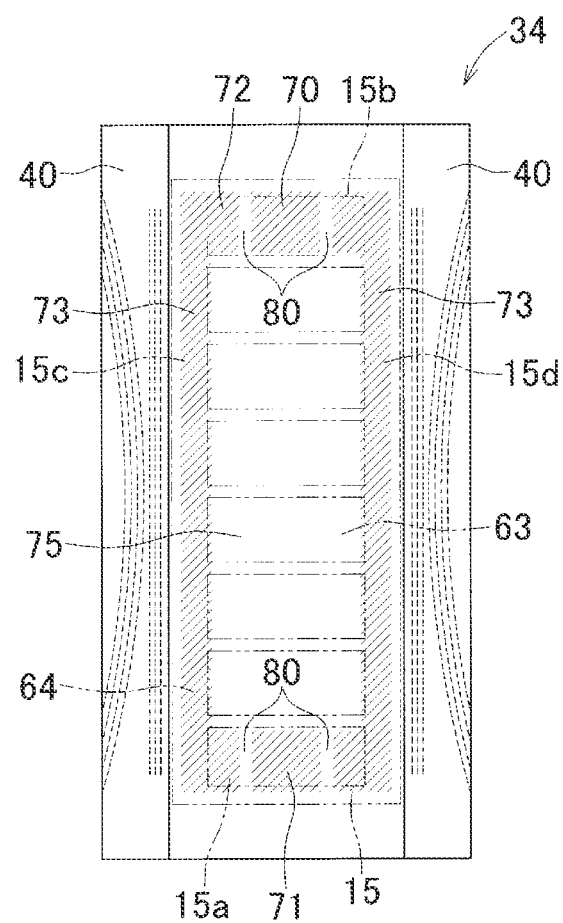
FIG. 8 is a plan view similar to FIG. 7, illustrating a second embodiment.

FIG. 8 is a folded plan view of the crotch layered sheet 34 similar to FIG. 7, illustrating a second embodiment of this invention. The basic construction of the diaper 10 according to second through fourth embodiments is substantially similar to that of the first embodiment and only features distinguished from those in the first embodiment will be described hereunder.

According to this embodiment, the opposite end bonding zones 71, 72 respectively include a pair of non-bonding regions 80 not coated with hot melt adhesive. These non-bonding regions 80 are provided in the form of narrow regions extending in the direction of the longitudinal axis and communicating with the central non-bonding region 75, i.e., each non-bonding region 80 extends through the entire width W1 of the corresponding end bonding zone 71 or 72.

In the opposite end bonding zones 71, 72, the liquid-absorbent structure 15 is planarly and continuously attached to the inner surface of the crotch laminar sheet 34 and, in consequence, stiffness in these regions is relatively high and these regions might not smoothly conform to the wearer's body shape. According to this embodiment, however, the opposite end bonding zones 71, 72 are partially formed with the non-bonding regions 80 adapted to alleviate the stiffness in these end segment bonding regions and thereby to ensure these regions to conform to the wearer's body shape. In addition, during use of the diaper 10, these non-bonding regions 80 communicate with the central non-bonding region 75 and function as air pathways serving to let the air into the central non-bonding region 75 from the outside so as to maintain the space S2 defined between the crotch layered sheet 34 and the liquid-absorbent structure 15 in an adequate volume. In this way, the liquid-absorbent structure 15 can be further spaced from the crotch layered sheet 34 and thereby the possibility that the absorbing regions 63 might be visually recognized from the outside may be further restricted. In this regard, it is possible to form at least one of the opposite end bonding zones 71, 72 with the non-bonding regions 80 or to form each of the opposite end bonding zones 71, 72 with a single non-bonding region 80 or more than two non-bonding regions 80 so long as the desired effect may be obtained.

Third Embodiment

Figure 9:
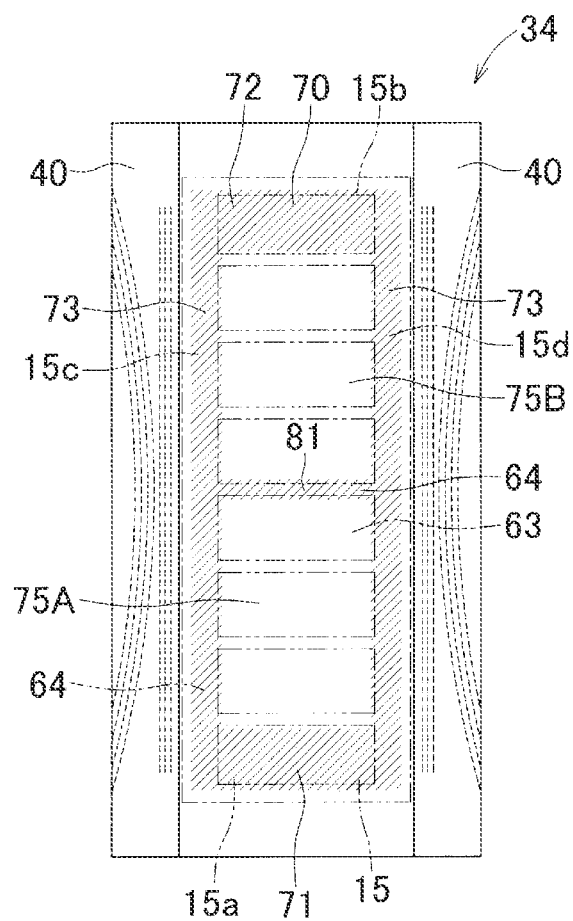
FIG. 9 is a plan view similar to FIG. 7, illustrating a third embodiment.

FIG. 9 is a folded plan view of the crotch layered sheet 34 similar to FIG. 7, illustrating a third embodiment of this invention.

According to this embodiment, the liquid-absorbent structure bonding region 70 further includes a traversing linear bonding region 81 extending in the direction of the transverse axis Q to partition the central non-bonding region 75 and thereby to define a front non-bonding sub-region 75A extending from this traversing linear bonding region 81 into the front waist region 11 and a rear non-bonding sub-region 75B extending from this traversing linear bonding region 81 into the rear waist region 12. The traversing linear bonding region 81 ensures the liquid-absorbent structure 15 to be more stably attached to the crotch layered sheet 34 in the central portion of the crotch region 13 and, in consequence, the liquid-absorbent structure 15 is unlikely to be peeled off from the crotch layered sheet 34 during use of the article. In addition, as is illustrated, the traversing linear bonding region 81 is formed to overlap the sealing region 64 and consequently the configuration of the absorbing regions 63 is unlikely to be visually recognized from the outside. It is not essential to form the traversing linear bonding region 81 in the vicinity of a middle region of the liquid-absorbent structure 15 as viewed in the direction of the longitudinal axis P and it is also possible to form this traversing linear bonding region 81 to be displaced toward one of the front and rear waist regions 11, 12. In some modifications, the traversing bonding region 81 is not necessarily linear.

Fourth Embodiment

Figure 10:
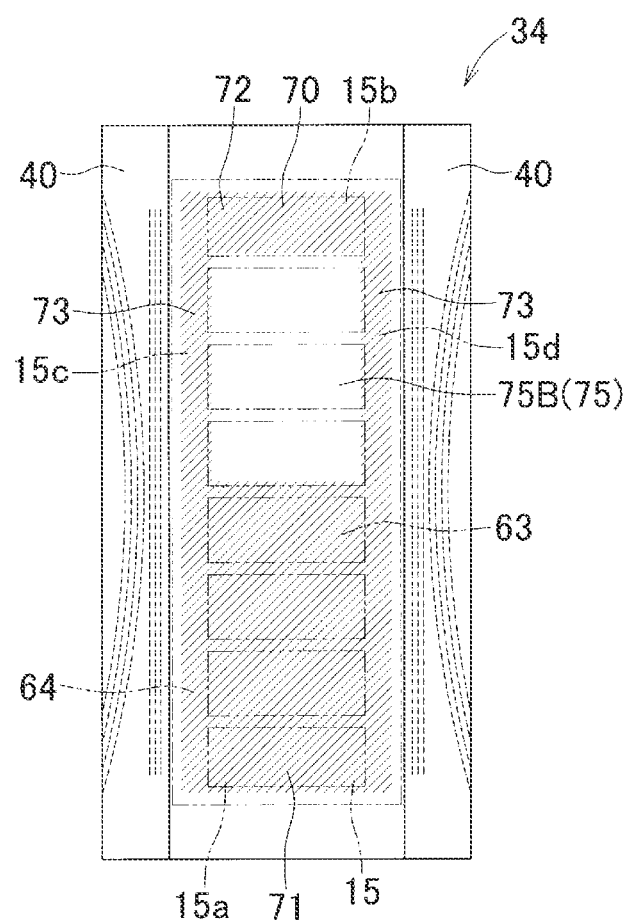
FIG. 10 is a plan view similar to FIG. 7, illustrating a fourth embodiment.

FIG. 10 is a folded plan view of the crotch layered sheet 34 similar to FIG. 7, illustrating a fourth embodiment of this invention.

According to this embodiment, one of the end bonding zones 71 extends to the region corresponding to the front non-bonding sub-region 75A, i.e., to the vicinity of the middle region of the liquid-absorbent structure 15 as viewed in the direction of the longitudinal axis P and the central segment 34A of the crotch layered sheet 34 is formed with the rear non-bonding sub-region 75B only. While the central non-bonding region 75 is provided for the purpose of preventing the configuration of the absorbing regions 63 having absorbed bodily fluids from being easily visually recognized from the outside, a relatively large amount of bodily fluids is discharged usually in the rear waist region 12 rather than in the front waist region 11. In other words, there is the possibility higher in the rear waist region 12 than in the front waist region 11 that the configuration of the absorbing regions 63 having absorbed bodily fluids might be visually recognized from the outside with ease. By forming at least the rear non-bonding sub-region 75B, the possibility that the diaper might be disfigured can be correspondingly restricted. In this regard, an alternative arrangement may be contemplated such that the other end bonding zone 72 extends to the rear non-bonding sub-region 75B and only the front non-bonding sub-region 75A is formed, depending on a purpose of use of the diaper 10.

The component members of the diaper 10 are not limited to those described in the specification but the other various types of material widely used in the relevant technical field may be used without limitation unless otherwise stated. The terms "first" and "second" used in the specification and claims of this application are used merely to distinguish similar elements, similar positions or similar means.

The aspect(s) of the present invention described above may be arranged in at least the following features:

(i) A disposable wearing article having a longitudinal axis and a transverse axis being orthogonal to the longitudinal axis, the article including:

a chassis including a skin-facing side, a non-skin-facing side, a front waist region, a rear waist region and a crotch region extending between the front and rear waist regions; and a liquid-absorbent structure attached to the skin-facing side of the chassis to lie in the crotch region, wherein:

the liquid-absorbent structure has front and rear ends extending in a direction of the transverse axis and opposite side edges extending in a direction of the longitudinal axis between the front and rear ends;

the liquid-absorbent structure is attached to the chassis by means of a liquid-absorbent structure bonding region;

the liquid-absorbent structure bonding region includes opposite end bonding zones and opposite lateral bonding zones, and a central non-bonding region is surrounded by the opposite end bonding zones and the opposite lateral bonding zones; and a central area of the liquid-absorbent structure corresponding to the central non-bonding region is free of direct attachment to the chassis.

The aspects described in the above item (i) may include at least the following embodiments, which may be taken in isolation or in combination with one another:

(ii) A width dimension of the opposite end bonding zones in the direction of the longitudinal axis is larger than a width dimension of the opposite lateral bonding zones in the direction of the transverse axis, and the liquid-absorbent structure is planarly and continuously attached to the chassis in the opposite end bonding zones.

(iii) The liquid-absorbent structure bonding region further includes at least one non-bonding region communicating with the central non-bonding region.

(iv) The liquid-absorbent structure bonding region further includes a traversing bonding sub-region extending in the direction of the transverse axis.

(v) One of the opposite end bonding zones in the liquid-absorbent structure bonding region extends to a middle region of the liquid-absorbent structure as viewed in the direction of the longitudinal axis.

(vi) The liquid-absorbent structure has a liquid-permeable sheet wrapping therein water-absorbent polymer particles, and includes at least one absorbing region containing therein the water-absorbent polymer particles and a sealing region surrounding the absorbing region.

(vii) A sub-region of the liquid-absorbent structure bonding region overlapping the absorbing region has an area in a range of about 0 to about 50% of a total area of the absorbing region.

(viii) A plurality of the absorbing regions are formed and the liquid-absorbent structure bonding region does not overlap sealing regions defined between respective pairs of the absorbing regions being adjacent to each other in the direction of the longitudinal axis.

(ix) The liquid-absorbent structure bonding region is formed of adhesive applied to this region.

(x) A thickness dimension of the crotch region measured in a midsection thereof including the liquid-absorbent structure is about 5.0 mm or less.

(xi) A sheet member defining the crotch region of the chassis has a total luminous transmittance of about 40% or less.

The described aspects and/or embodiments provide one or more of the following effects:

In the disposable wearing article according to some embodiments of this invention, the liquid-absorbent structure bonding region in which the liquid-absorbent structure is attached to the chassis has the opposite end bonding zones and the opposite lateral bonding zones, and the central non-bonding region is defined by the region surrounded by the opposite end bonding zones and the opposite lateral bonding zones. This arrangement ensures that the portion of the liquid-absorbent structure opposed to the central non-bonding region is spaced from the chassis during use of the article. Consequentially, after bodily fluids have been excreted, the configuration of the absorbing region in the liquid-absorbent structure may hardly be visually recognized from the outside and the disposable wearing article would not be disfigured.

This application claims the benefit of Japanese Application No. 2011-142354 the entire disclosure of which is incorporated by reference herein.

The invention claimed is:
1. A disposable wearing article having a longitudinal axis and a transverse axis being orthogonal to the longitudinal axis, the article comprising:
a chassis including a skin-facing side, a non-skin-facing side, a front waist region, a rear waist region, and a crotch region extending between the front and rear waist regions; and
a liquid-absorbent structure attached to the skin-facing side of the chassis to lie in the crotch region,
wherein:
the liquid-absorbent structure has
front and rear ends extending in a transverse direction of the transverse axis and
opposite side edges extending in a longitudinal direction of the longitudinal axis between the front and rear ends,
the liquid-absorbent structure further includes
first and second sheets opposing each other in a thickness direction perpendicular to the longitudinal direction and the transverse direction;
absorbing regions including water-absorbent polymer particles between the first sheet and the second sheet, and
sealing regions surrounding the absorbing regions, wherein the first and second sheets are bonded to each other in said sealing regions; and
a liquid-absorbent structure bonding region attached to the chassis,
the liquid-absorbent structure bonding region includes opposite end bonding zones, opposite lateral bonding zones,
a central non-bonding region is surrounded by the opposite end bonding zones and the opposite lateral bonding zones,
the opposite lateral bonding zones of the liquid-absorbent structure bonding region overlap the sealing regions in the thickness direction, and
a central area of the second sheet of the liquid-absorbent structure corresponding to the central non-bonding region is free of direct attachment to the chassis.

2. The wearing article defined by claim 1, wherein
a dimension of each of the opposite end bonding zones in the longitudinal direction is larger than a dimension of each of the opposite lateral bonding zones in the transverse direction, and
the liquid-absorbent structure is planarly and continuously attached to the chassis in the opposite end bonding zones.

3. The wearing article defined by claim 1, wherein the liquid-absorbent structure further includes at least one non-bonding region extending in the longitudinal direction through the opposite end bonding zones, said at least one non-bonding region connecting with the central non-bonding region.

4. The wearing article defined by claim 1, wherein the liquid-absorbent structure bonding region further includes a traversing bonding sub-region extending in the transverse direction and connecting with the opposite lateral bonding zones.

5. The wearing article defined by claim 1, wherein one of the opposite end bonding zones in the liquid-absorbent structure bonding region extends to a middle region of the liquid-absorbent structure as viewed in the longitudinal direction.

6. The wearing article defined by claim 1, wherein
the first and second sheets of the liquid-absorbent structure are liquid-permeable and wrapping therein the water-absorbent polymer particles.

7. The wearing article defined by claim 6, wherein a sub-region of the liquid-absorbent structure bonding region overlapping the absorbing regions has an area in a range of about 0 to about 50% of a total area of the absorbing regions.

8. The wearing article defined by claim 6, wherein
the absorbing regions include pairs of absorbing regions adjacent to each other in the longitudinal direction, and
the liquid-absorbent structure bonding region does not overlap sealing regions defined between the pairs of the absorbing regions in the thickness direction.

9. The wearing article defined by claim 1, wherein the liquid-absorbent structure bonding region includes adhesive.

10. The wearing article defined by claim 1, wherein a thickness dimension of the crotch region measured in a midsection thereof including the liquid-absorbent structure is about 5.0 mm or less.

11. The wearing article defined by claim 1, wherein a sheet member defining the crotch region of the chassis has a total luminous transmittance of about 40% or less.

12. The wearing article defined by claim 1, wherein
the crotch region includes a crotch layered sheet having a central segment corresponding to an area of the liquid-absorbent structure bonding region, and
lateral segments on opposite sides of the central segment in the transverse direction, and
each of the lateral segments is folded inward along a fold line extending in the longitudinal direction and is attached to itself by lateral elastic bonding zones to form lateral elastic segments.

13. The wearing article defined by claim 12, wherein the lateral elastic bonding zones include
first lateral elastic bonding zones located outboard of the opposite end bonding zones of the liquid-absorbent structure bonding region in the longitudinal direction; and
second lateral elastic bonding zones located outboard of the opposite lateral bonding zones of the liquid-absorbent structure bonding region in the transverse direction.

14. The wearing article defined by claim 13, wherein the lateral elastic segments include
first leg elastics rectilinearly extending in the longitudinal direction; and
second leg elastics extending in a curved state toward the front and rear waist regions.

15. The wearing article defined by claim 1, wherein the central area of the second sheet of the liquid-absorbent structure corresponding to the central non-bonding region is arranged between the opposite end bonding zones of the liquid-absorbent structure bonding region and is elongated in the longitudinal direction.

16. The wearing article defined by claim 15, wherein the central area of the second sheet of the liquid-absorbent structure overlaps at least one of the sealing regions and at least one of the absorbing regions in the thickness direction.

17. The wearing article defined by claim 1, wherein
the liquid-absorbent structure further comprises non-bonding regions which are not coated with adhesive and in which the liquid-absorbent structure is free of direct attachment to the chassis, and
the non-bonding regions extend in the longitudinal direction through the opposite end bonding zones to the central non-bonding region.

18. The wearing article defined by claim 1, wherein
the liquid-absorbent structure bonding region further includes a traversing linear bonding region extending in the transverse direction,
said traversing linear bonding region divides the central non-bonding region into
a front non-bonding sub-region extending in the longitudinal direction from the traversing linear bonding region into the front waist region, and
a rear non-bonding sub-region extending in the longitudinal direction from the traversing linear bonding region into the rear waist region, and
said traversing linear bonding region overlaps one of the sealing regions in the thickness direction.

* * * * *